United States Patent [19]

Glock et al.

[11] Patent Number: 5,618,774
[45] Date of Patent: Apr. 8, 1997

[54] SELECTIVE SAFENED HERBICIDAL COMPOSITION

[75] Inventors: Jutta Glock, Mumpf; Manfred Hudetz, Rheinfelden, both of Switzerland; Elmar Kerber, Görwihl, Germany

[73] Assignee: Ciba-Geigy Corporation, Tarrytown, N.Y.

[21] Appl. No.: 576,269

[22] Filed: Dec. 21, 1995

Related U.S. Application Data

[63] Continuation of Ser. No. 462,444, Jun. 5, 1995, abandoned, which is a continuation of Ser. No. 325,913, Oct. 19, 1994, abandoned.

[30] Foreign Application Priority Data

Dec. 8, 1993 [CH] Switzerland .................. 3658/93

[51] Int. Cl.⁶ .................. A01N 25/32; A01N 43/20; A01N 43/42; A01N 43/56
[52] U.S. Cl. .................. 504/105; 504/106
[58] Field of Search .................. 504/105, 106

[56] References Cited

U.S. PATENT DOCUMENTS

| | | | |
|---|---|---|---|
| 4,639,266 | 1/1987 | Heubach et al. | 71/92 |
| 4,902,340 | 2/1990 | Hubele | 71/94 |
| 4,944,790 | 7/1990 | Moser et al. | 71/92 |
| 5,023,333 | 6/1991 | Hubele | 546/175 |
| 5,078,780 | 1/1992 | Moser et al. | 71/92 |
| 5,102,445 | 4/1992 | Hubele | 71/94 |
| 5,114,462 | 5/1992 | Moser et al. | 71/88 |
| 5,209,771 | 5/1993 | Meyer | 504/178 |
| 5,350,734 | 9/1994 | Glock et al. | 504/105 |
| 5,371,060 | 12/1994 | Glock et al. | 504/106 |
| 5,488,027 | 1/1996 | Bauer et al. | 504/105 |

FOREIGN PATENT DOCUMENTS 9317016  9/1993  WIPO .

OTHER PUBLICATIONS

Derwent abstract No. 93-274851/35 for EP558448-A1 1993.

*Primary Examiner*—S. Mark Clardy
*Attorney, Agent, or Firm*—Marla J. Mathias; William A. Teoli, Jr.

[57] ABSTRACT

A selective herbicidal composition for controlling grasses and weeds in crops of cultivated plants, comprising, in addition to inert carriers and adjuvants, as active component a mixture of
a) a herbicidally effective mount of a N-phenylsulfonyl-N'-triazinylurea of formula I

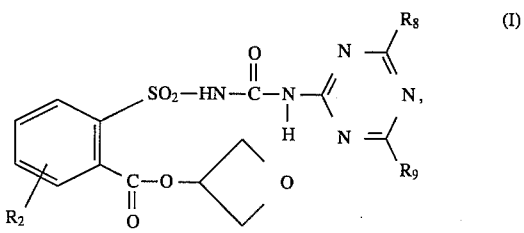

wherein the substituents are as defined in claim 1, and
b) to antagonise the herbicide, an antidotally effective mount of a quinoline derivative of formula IIa

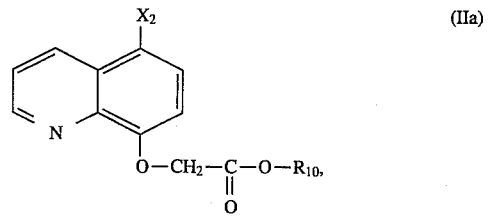

wherein
$R_{10}$ is hydrogen, $C_1$-$C_8$alkyl or $C_1$-$C_8$alkyl which is substituted by $C_1$-$C_6$alkoxy or $C_3$-$C_6$alkenyloxy; and
$X_2$ is hydrogen or chloro; or of a 1-phenylazole-3-carboxylic acid derivative of formula IIb

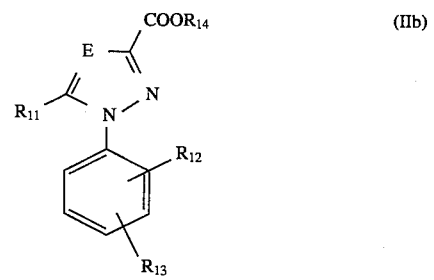

wherein
E is nitrogen or methine;
$R_{11}$ is —$CCl_3$, phenyl or halogen-substituted phenyl;
$R_{12}$ and $R_{13}$ are each independently of the other hydrogen or halogen; and $R_{14}$ is $C_1$-$C_4$alkyl.

10 Claims, No Drawings

SELECTIVE SAFENED HERBICIDAL COMPOSITION

This application is a continuation of Ser. No. 08/462,444 filed Jun. 5, 1995, abandoned which is a continuation of Ser. No. 08/325,913 filed Oct. 19, 1994, now abandoned.

The present invention relates to a selective herbicidal composition for controlling grasses and weeds in crops of cultivated plants, especially in crops of cereals, which composition comprises a herbicide and a safener (antidote) and protects the cultivated plants, but not the weeds, from the phytotoxic action of the herbicide, and to the use of said composition for controlling weeds in crops of cultivated plants.

When applying herbicides, the cultivated plants may also suffer severe damage owing to factors that include the concentration of the herbicide and the mode of application, the cultivated plant itself, the nature of the soil, and the climatic conditions such as exposure to light, temperature and rainfall.

To counteract this problem and similar ones, the proposal has already been made to use different compounds as safeners which are able to antagonise the harmful action of the herbicide on the cultivated plant, i.e. to protect the cultivated plant while leaving the herbicidal action on the weeds to be controlled virtually unimpaired. It has, however, been found that the proposed safeners often have a very specific action, not only with respect to the cultivated plants but also to the herbicide, and in some cases also subject to the mode of application, i.e. a specific safener will often be suitable only for a specific cultivated plant and a specific class of herbicide or a specific herbicide.

Thus, for example, EP-A-0 094 349 discloses quinoline derivatives that protect cultivated plants from the phytotoxic action of herbicides, including phenoxypropionate herbicides, ureas, carbamates or diphenyl ethers. EP-A-0 558 448 discloses 1-phenylazole-3-carboxylic acid derivatives for protecting cultivated plants from the phytotoxic action of sulfonylureas.

It has now been found that very special safeners selected from the classes of the quinoline derivatives and 1-phenylazole-3-carboxylic acid derivatives are suitable for protecting cultivated plants from the phytotoxic action of a certain class of N-phenylsulfonyl-N'-triazinylurea herbicides.

Accordingly, the invention provides a selective herbicidal composition comprising, in addition to inert formulation assistants such as carriers, solvents and wetting agents, as active component a mixture of
a) a herbicidally effective amount of a N-phenylsulfonyl-N'-triazinylurea of formula I

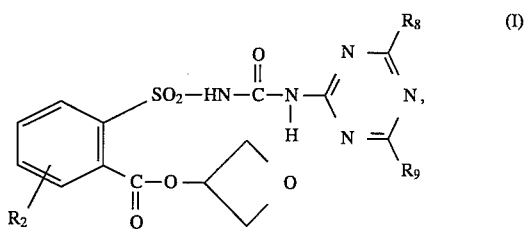

wherein
$R_2$ is hydrogen, fluoro, chloro, bromo, iodo, $(X)_n R_3$, $NO_2$, $NR_4 R_5$, $-C \equiv CR_6$,

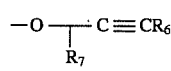

or cyano;
n is 0 or 1;
$R_3$ is $C_1$-$C_4$alkyl or $C_1$-$C_4$alkyl which is substituted by 1 to 4 halogen atoms, $C_1$-$C_3$alkoxy or $C_1$-$C_3$alkylthio; $C_2$-$C_4$alkenyl or $C_2$-$C_4$alkenyl which is substituted by 1 to 4 halogen atoms,
$R_4$ is hydrogen, $CH_3O$, $CH_3CH_2O$ or $C_1$-$C_3$alkyl;
$R_5$ is hydrogen or $C_1$-$C_3$alkyl;
$R_6$ is hydrogen, methyl or ethyl;
$R_7$ is hydrogen or methyl;
$R_8$ is $C_1$-$C_4$alkyl, $C_1$-$C_4$alkoxy, $C_1$-$C_4$haloalkoxy, $C_1$-$C_4$haloalkyl, $C_1$-$C_4$haloalkylthio, $C_1$-$C_4$alkylthio, halogen, $C_2$-$C_5$alkoxyalkyl, $C_2$-$C_5$alkoxyalkoxy, amino, $C_1$-$C_3$alkylamino or di($C_1$-$C_3$alkyl)amino; and
$R_9$ is $C_1$-$C_4$alkyl, $C_1$-$C_4$alkoxy, $C_1$-$C_4$haloalkoxy, $C_1$-$C_4$haloalkylthio, $C_1$-$C_4$alkylthio, $C_2$-$C_5$alkoxyalkyl, $C_2$-$C_5$alkoxyalkoxy, $C_2$-$C_5$alkylthioalkyl or cyclopropyl; with the proviso that $R_8$ and $R_9$ are not $OCHF_2$ and $SCHF_2$; and
b) as safener to antagonise the herbicide, an antidotally effective amount of either a quinoline derivative of formula IIa

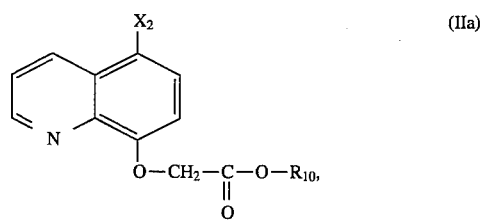

wherein
$R_{10}$ is hydrogen, $C_1$-$C_8$alkyl or $C_1$-$C_8$alkyl which is substituted by $C_1$-$C_6$alkoxy or $C_3$-$C_6$alkenyloxy; and
$X_2$ is hydrogen or chloro; or of a 1-phenylazole-3-carboxylic acid derivative of formula IIb

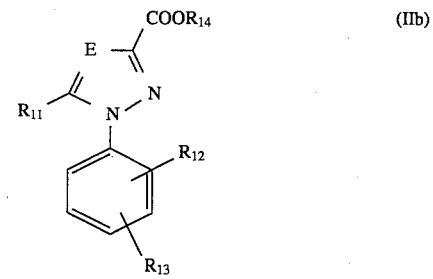

wherein
E is nitrogen or methine;
$R_{11}$ is $-CCl_3$, phenyl or halogen-substituted phenyl;
$R_{12}$ and $R_{13}$ are each independently of the other hydrogen or halogen; and $R_{14}$ is
$C_1$-$C_4$alkyl; with the proviso that $R_2$ is not hydrogen if the safener consists of a compound of formula IIb.

The alkyl groups occurring the definitions of the substituents may be straight-chain or branched and are typically methyl, ethyl, n-propyl, isopropyl, n-butyl, see-butyl, isobutyl or tert-butyl. The alkyl groups preferably contain 1 to 3 carbon atoms.

Halogen in the above definitions will be taken to mean fluoro, chloro, bromo and iodo. Fluoro, chloro and bromo are preferred.

Alkenyl will be taken to mean straight-chain or branched alkenyl and is typically vinyl, allyl, methallyl, 1-methylvinyl or but-2-en-1-yl. Alkenyl groups having a chain length of 2 to 3 carbon atoms are preferred.

Haloalkyl will typically be fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl; preferably trichloromethyl, difluorochloromethyl, trifluoromethyl and dichlorofluoromethyl.

Alkoxy is typically methoxy, ethoxy, propoxy, isopropoxy, n-butoxy, isobutoxy, sec-butoxy and ten-butoxy; preferably methoxy and ethoxy.

Haloalkoxy is typically difluoromethoxy, trifluoromethoxy, 2,2,2-trifluoroethoxy, 1,1,2,2-tetrafluoroethoxy, 2-fluoroethoxy, 2-chloroethoxy and 2,2-difluoroethoxy. Difluoromethoxy, 2-chloroethoxy and trifluoromethoxy are preferred.

Alkylthio is is typically methylthio, ethylthio, propylthio, isopropylthio, n-butylthio, isobutylthio, sec-butylthio or tert-butylthio, preferably methylthio and ethylthio.

Typical examples of alkoxyalkoxy are: methoxymethoxy, methoxyethoxy, methoxypropoxy, ethoxymethoxy, ethoxyethoxy and propoxymethoxy.

Alkylamino is is typically methylamino, ethylamino, n-propylamino or isopropylamino. Dialkylamino is typically dimethylamino, methylethylamino, diethylamino or n-propylmethylamino.

The invention also embraces the salts which the compounds of formula I are able to form with amines, alkali metal and alkaline earth metal bases or quaternary ammonium bases.

Preferred alkali metal and alkaline earth metal hydroxides as salt formers are the hydroxides of lithium, sodium, potassium, magnesium or calcium, most preferably those of sodium or potassium.

Illustrative examples of amines suitable for forming ammonium cations are ammonia as well as primary, secondary and tertiary $C_1$-$C_{18}$alkylamines, $C_1$-$C_4$hydroxyalkylamines and $C_2$-$C_4$alkoxyalkylamines typically methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methyl ethylamine, methyl isopropylamine, methyl hexylamine, methyl nonylamine, methyl pentadecylamine, methyl octadecylamine, ethyl butylamine, ethyl heptylamine, ethyl octylamine, hexyl heptylamine, hexyl octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines such as pyridine, quinoline, isoquinoline, morpholine, piperidine, pyrrolidine, indoline, quinuclidine and azepine; primary arylamines such as anilines, methoxyanilines, ethoxyanilines, o-, m- and p-toluidines, phenylenediamines, benzidines, naphthylamines and o-,m- and p-chloroanilines; but preferably triethylamines, isopropylamine and diisopropylamine.

Preferred compounds of formula I or salts thereof for use in the compositions of this invention are those wherein $R_8$ is methyl and $R_9$ is methoxy.

Those compositions are also preferred which contain a safener of formula IIa. Among these safeners, those compounds are particularly preferred in which $X_2$ is chloro, and $R_{10}$ is preferably the group —CH(CH$_3$)—C$_5$H$_{11}$—n or —CH(CH$_3$)—CH$_2$—O—CH$_2$CH═CH$_2$. Very particularly preferred compositions of this invention contain a compound of formula IIe

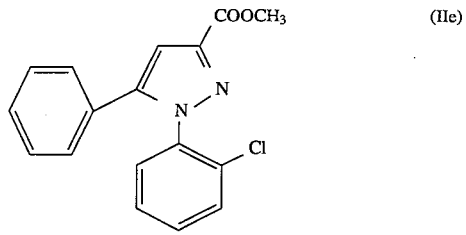

as safener.

Preferred compounds of formula I are listed in the following Table 1 as compounds of formula Ib.

TABLE 1

Compounds of formula Ib:

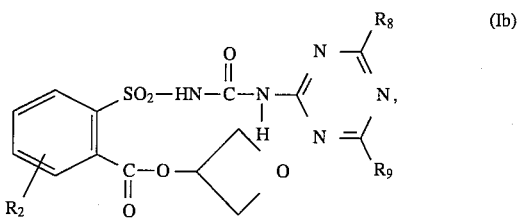

| Cmpd. No. | $R_2$ | $R_8$ | $R_9$ |
|---|---|---|---|
| 1.01 | H | CH$_3$ | OCH$_3$ |
| 1.02 | 5-Cl | CH$_3$ | OCH$_3$ |
| 1.03 | 5-OCH$_3$ | CH$_3$ | OCH$_3$ |
| 1.04 | 5-OC$_2$H$_5$ | CH$_3$ | OCH$_3$ |
| 1.05 | 5-F | CH$_3$ | OCH$_3$ |
| 1.06 | 4-F | CH$_3$ | OCH$_3$ |
| 1.07 | 4-Cl | CH$_3$ | OCH$_3$ |
| 1.08 | 5-OCH$_3$ | OCH$_3$ | OCH$_3$ |
| 1.09 | 5-OCHF$_2$ | CH$_3$ | OCH$_3$ |

Preferred compounds of formula IIa are listed in the following Table 2:

TABLE 2

Compounds of formula IIa:

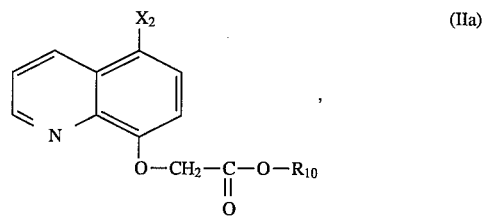

| Cmpd. No. | $X_2$ | $R_{10}$ |
|---|---|---|
| 2.01 | Cl | —CH(CH$_3$)—C$_5$H$_{11}$-n |
| 2.02 | Cl | —CH(CH$_3$)—CH$_2$OCH$_2$CH═CH$_2$ |
| 2.03 | Cl | H |
| 2.04 | Cl | C$_4$H$_9$-n |

Preferred compounds of formula IIb are listed in the following Table 3:

TABLE 3

Compounds of formula IIb:

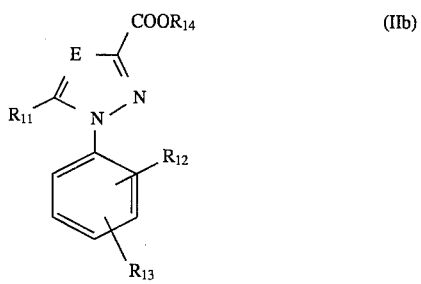

(IIb)

| Cmpd. No. | $R_{14}$ | $R_{11}$ | $R_{12}$ | $R_{13}$ | E |
|---|---|---|---|---|---|
| 3.01 | $CH_3$ | phenyl | 2-Cl | H | CH |
| 3.02 | $CH_3$ | phenyl | 2-Cl | 4-Cl | CH |
| 3.03 | $CH_3$ | phenyl | 2-F | H | CH |
| 3.04 | $CH_3$ | 2-chlorophenyl | 2-F | H | CH |
| 3.05 | $C_2H_5$ | $CCl_3$ | 2-Cl | 4-Cl | N |
| 3.06 | $CH_3$ | phenyl | 2-Cl | 4-$CF_3$ | N |
| 3.07 | $CH_3$ | phenyl | 2-Cl | 4-$CF_3$ | N |

Preferred novel combinations of herbicide-safener are listed in Table 4:

TABLE 4

Preferred combinations of herbicide-safener:

| | | | |
|---|---|---|---|
| 1.01 + 2.01 | 1.01 + 2.02 | 1.01 + 2.03 | 1.01 + 2.04 |
| 1.02 + 2.03 | 1.03 + 2.03 | 1.04 + 2.03 | |
| 1.05 + 2.01 | 1.05 + 2.02 | 1.05 + 2.03 | 1.05 + 2.04 |
| 1.06 + 2.01 | 1.06 + 2.02 | 1.06 + 2.03 | 1.06 + 2.04 |
| 1.07 + 2.01 | 1.07 + 2.02 | 1.07 + 2.03 | 1.07 + 2.04 |
| 1.01 + 3.01 | 1.01 + 3.02 | 1.01 + 3.03 | 1.01 + 3.04 |
| 1.01 + 3.05 | 1.01 + 3.06 | 1.01 + 3.07 | |
| 1.02 + 3.01 | 1.02 + 3.02 | 1.02 + 3.03 | 1.02 + 3.04 |
| 1.02 + 3.05 | 1.02 + 3.06 | 1.02 + 3.07 | |
| 1.03 + 3.02 | 1.03 + 3.03 | 1.03 + 3.04 | 1.03 + 3.06 |
| 1.04 + 3.01 | 1.04 + 3.02 | 1.04 + 3.03 | 1.04 + 3.04 |
| 1.04 + 3.05 | 1.04 + 3.06 | 1.04 + 3.07 | |
| 1.05 + 3.01 | 1.05 + 3.02 | 1.05 + 3.03 | 1.05 + 3.04 |
| 1.05 + 3.05 | 1.05 + 3.06 | 1.05 + 3.07 | |
| 1.06 + 3.01 | 1.06 + 3.02 | 1.06 + 3.03 | 1.06 + 3.04 |
| 1.06 + 3.05 | 1.06 + 3.06 | 1.06 + 3.07 | |
| 1.07 + 3.01 | 1.07 + 3.02 | 1.07 + 3.03 | 1.07 + 3.04 |
| 1.07 + 3.05 | 1.07 + 3.06 | 1.07 + 3.07 | |
| 1.02 + 2.01 | 1.02 + 2.02 | 1.02 + 2.04 | 1.03 + 2.01 |
| 1.03 + 2.02 | 1.03 + 2.04 | 1.04 + 2.01 | 1.04 + 2.02 |
| 1.04 + 2.04 | 1.03 + 3.01 | 1.03 + 3.05 | 1.03 + 3.07 |

The compounds of formulae I, IIa and IIb are known or they can be prepared by methods analogous to known ones. Compounds of formula I are disclosed, inter alia, in U.S. Pat. No. 5,209,771.

The quinoline derivatives falling within the scope of formula IIa and the preparation thereof are known or can be prepared by methods analogous to known ones, inter alia those disclosed in EP-A-0 094 349. Compounds of formula IIb are disclosed in EP-A-0 268 554 and EP-A-0 174 562.

The invention also relates to a method of selectively controlling weeds in crops of cultivated plants, which comprises treating said cultivated plants, the seeds or seedlings or the crop area thereof, concurrently or separately, with a herbicidally effective amount of the pyrimidine of formula I and, to antagonise the herbicide, an antidotally effective mount of a safener of formula IIa or IIb.

Suitable cultivated plants which can be protected by the safener of formula IIa or IIb against the harmful action of the aforementioned herbicides are preferably those important in the food or textile sector, typically sugar cane and, in particular, millet, maize, rice and cereals (wheat, rye, barley, oats). It is very particularly preferred to use the novel composition in crops of cereals.

The weeds to be controlled may be monocot as well as dicot weeds.

Crop plants or parts of said plants are typically those referred to above. Crop areas are the areas already under cultivation with the crop plants or seeds thereof, as well as the areas intended for cultivation with said crop plants.

Depending on the end use, a safener of formula IIa or IIb can be used for pretreating seeds of the crop plants (dressing of seeds of seedlings) or it can be incorporated in the soil before or after sowing. It can, however, also be applied by itself alone or together with the herbicide pre- or postemergence. Treatment of the plant or the seeds with the safener can therefore in principle be carried out irrespective of the time of application of the phytotoxic chemical. Treatment of the plant can, however, also be carried out by simultaneous application of the phytotoxic chemical and safener (tank mixture). The pre-emergence treatment includes treatment of the crop area before sowing as well as treatment of the crop area after sowing but before emergence of the plants.

The concentration of safener to be applied with respect to the herbicide will depend substantially on the mode of application. Where a field treatment is carded out either by using a tank mixture with a combination of safener and herbicide or by separate application of safener and herbicide, the ratio of safener to herbicide will usually be from 1:100 to 10:1, preferably from 1:20 to 1:1, and specifically 1:1. On the other hand, for seed dressing much lower concentrations of safener are required in comparison to the concentration of herbicide per hectare of cultivated area.

In field treatment, 0.001 to 5.0 kg/ha, preferably 0.01 to 0.5 kg/ha, of safener, will usually be applied.

The concentration of herbicide is usually in the range from 0.001 to 2 kg/ha, but will preferably be from 0.05 to 1 kg/ha.

For seed dressing, 0.001 to 10 g of safener/kg of seeds, preferably 0.05 to 2 g of safener/kg of seeds, is usually applied. If the safener is used in liquid form shortly before sowing to effect soaking, then it is preferred to use safener solutions that contain the active ingredient in a concentration of 1 to 10 000 ppm, preferably of 100 to 1000 ppm.

For application, it is preferred to process the compounds of formula II, or combinations of the compounds of formula IIa or IIb and the herbicides of formula I to be antagonised, together with the assistants conventionally employed in formulation technology, to coatable pastes, directly sprayable or dilutable solutions, dilute emulsions, wettable powders, soluble powders, dusts, granulates or and also encapsulations in e.g. polymer substances. As with the type of compositions, the methods of application such as spraying, atomising, dusting, scattering coating or pouring, are chosen in accordance with the intended objectives and the prevailing circumstances.

The formulations, i.e. the compositions, preparations or mixtures containing the compound of formula IIa or IIb or a combination of formula IIa or IIb with the herbicide of formula I to be antagonised and, where appropriate, a solid or liquid adjuvant, are prepared in known manner, e.g. by homogeneously mixing and/or grinding the active ingredients with extenders, typically with solvents, solid carriers and, in some cases, surface-active compounds (surfactants).

Suitable solvents may typically be: aromatic hydrocarbons, preferably the fractions containing 8 to 12 carbon atoms, for example xylene mixtures or substituted naphthalenes; phthalates such as dibutyl or dioctyl phthalate; aliphatic hydrocarbons such as cyclohexane or paraffins; alcohols and glycols and their ethers and esters, for example ethanol, diethylene glycol, 2-methoxyethanol or 2-ethoxyethanol; ketones such as cyclohexanone; strongly polar solvents such as N-methyl-2-pyrrolidone, dimethyl sulfoxide or dimethyl formamide; as well as vegetable oils or epoxidised vegetable oils such as epoxidised coconut oil or soybean oil; or water.

The solid carriers typically used for dusts and dispersible powders are usually natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, including pumice, broken brick, sepiolite or bentonite; and suitable nonsorbent carriers are materials such as calcite or sand. In addition, innumerable pregranulated materials of inorganic or organic origin may be used, especially dolomite or pulverised plant residues.

Depending on the safener of formula IIa or IIb to be formulated, and usually also on the herbicide, suitable surface-active compounds are nonionic, cationic and/or anionic surfactants having good emulsifying, dispersing and wetting properties. Surfactants will also be understood as comprising mixtures of surfactants.

Suitable anionic surfactants may be water-soluble soaps as well as water-soluble synthetic surface-active compounds.

Suitable soaps are the alkali metal salts, alkaline earth metal salts, ammonium salts or substituted ammonium salts of higher fatty acids ($C_{10}$-$C_{22}$), e.g. the sodium or potassium salts of oleic or stearic acid, or of mixtures of natural fatty acids which can be obtained, inter alia, from coconut oil or tallow oil. Further suitable soaps are also the fatty acid methyl taurin salts.

More often, however, so-called synthetic surfactants are used, especially fatty sulfonates, fatty sulfates, sulfonated benzimidazole derivatives or alkylarylsulfonates.

The fatty alcohol sulfonates or sulfates are usually in the form of alkali metal salts, alkaline earth metal salts, ammonium salts or substituted ammonium salts, and they contain a $C_8$-$C_{22}$alkyl radical which also includes the alkyl moiety of acyl radicals, e.g. the sodium or calcium salt of ligninsulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Corresponding phosphates, typically salts of the phosphoric acid ester of an adduct of p-nonylphenol with 4 to 14 mol of ethylene oxide, or phospholipids, are also suitable.

Nonionic surfactants are preferably polyglycol ether derivatives of aliphatic or cycloaliphatic alcohols or of saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are nonylphenol polyethoxylates, polyethoxylated castor oil, polyadducts of polypropylene and polyethylene oxide, tributylphenol polyethoxylate, polyethylene glycol and octylphenol polyethoxylate.

Fatty acid esters of polyoxyethylene sorbitan are also suitable nonionic surfactants, typically polyoxyethylene sorbitan trioleate.

Cationic surfactants are preferably quaternary ammonium salts carrying, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl)ethylammonium bromide.

The surfactants customarily employed in the art of formulation are described, inter alia, in "Mc Cutcheon's Detergents and Emulsifiers Annual", MC Publishing Corp., Glen Rock, N.J., 1981, H. Stache, "Tensid-Taschenbuch" (Handbook of Surfactants), Carl Hanser Verlag, Munich/Vienna 1981.

The agrochemical compositions will usually contain from 0.1 to 99% by weight, preferably from 0.1 to 95% by weight, of safener of formula IIa or IIb or mixture of safener and herbicide, from 1 to 99.9% by weight, preferably from 5 to 99.8% by weight, of a solid or liquid formulation assistant, and from 0 to 25% by weight, preferably from 0.1 to 25% by weight, of a surfactant.

Whereas it is preferred to formulate commercial products as concentrates, the end user will normally use dilute formulations.

The compositions may also contain further ingredients such as stabilisers, antifoams, viscosity regulators, binders, tackifiers, as well as fertilisers or other chemical agents for achieving special effects.

Different methods and techniques may suitably be used for applying the safeners of formula IIa or IIb or compositions containing them for protecting cultivated plants from the harmful effects of herbicides of formula I, conveniently the following:

i) Seed dressing a) Dressing the seeds with a wettable powder formulation of the compound of formula IIa or IIb by shaking in a vessel until the safener is uniformly distributed on the surface of the seeds (dry treatment), using up to c. 1 to 500 g of compound of formula IIa or IIb (4 g to 2 g of wettable powder) per 100 kg of seeds.

b) Dressing seeds with an emulsifiable concentrate of the compound of formula IIa or IIb by method a) (wet treatment).

c) Dressing by immersing the seeds in a mixture containing 100–1000 ppm of compound of formula IIa or IIb for 1 to 72 hours, leaving them wet or subsequently drying them (seed soaking).

Seed dressing or treatment of the germinated seedlings are naturally the preferred methods of application, as the safener treatment is fully concentrated on the target crop. Usually 1 to 1000 g, preferably 5 to 250 g, of safener is used per 100 kg of seeds. However, depending on the method employed, which also permits the use of other chemical agents or micronutrients, plus or minus deviations from the indicated limiting concentrations are possible (repeat dressing).

ii) Application from a tank mixture

A liquid formulation of a mixture of safener and herbicide (reciprocal ratio from 10:1 to 1:100) is used, the concentration of herbicide being from 0.01 to 5.0 kg/ha. This tank mixture is applied before or after sowing.

iii) Application in the furrow

The safener formulated as emulsifiable concentrate, wettable powder or granulate is applied to the open furrow in which the seeds have been sown. After covering the furrow, the herbicide is applied pre-emergence in conventional manner.

iv) Controlled release of safener

A solution of the compound of formula IIa or IIb is applied to mineral granulate substrates or polymerised granulates (urea/formaldehyde) and allowed to dry. A coating may additionally be applied (coated granulates) which permits controlled release of the safener over a specific period of time.

Formulation Examples for mixtures of herbicides of formula I and safeners of formula IIa or IIb (throughout, percentages are by weight)

| F1. Solutions | a) | b) | c) | d) |
|---|---|---|---|---|
| compound mixture | 5% | 10% | 50% | 90% |
| 1-methoxy-3-(3-methoxypropoxy)-propane | — | 20% | 20% | — |
| polyethylene glycol 400 | 20% | 10% | — | — |
| N-methyl-2-pyrrolidone | — | — | 30% | 10% |
| mixture of aromatic hydrocarbons $C_9$–$C_{12}$ | 75% | 60% | — | — |

The solutions are suitable for use as microdrops.

| F2. Wettable powders | a) | b) | c) | d) |
|---|---|---|---|---|
| compound mixture | 5% | 25% | 50% | 80% |
| sodium ligninsulfonate | 4% | — | 3% | — |
| sodium laurylsulfate | 2% | 3% | — | 4% |
| sodium diisobutylnaphthalene sulfonate | — | 6% | 5% | 6% |
| octylphenol polyethoxylate (7–8 mol EO) | — | 1% | 2% | — |
| highly dispersed silica | 1% | 3% | 5% | 10% |
| kaolin | 88% | 62% | 35% | — |

The compound mixture is throughly mixed with the adjuvants and this mixture is ground in a suitable mill to give wettable powders which can be diluted with water to give suspensions of any desired concentration.

| F3. Coated granulates | a) | b) | c) |
|---|---|---|---|
| compound mixture | 0.1% | 5% | 15% |
| highly dispersed silica | 0.9% | 2% | 2% |
| inorganic carrier (⌀ 0.1–1 mm) e.g. CaCO$_3$ or SiO$_2$ | 99.0% | 93% | 83% |

The compound mixture is dissolved in methylene chloride, the solution is sprayed on to the carrier, and the solvent is removed under vacuum.

| F4. Coated granulates | a) | b) | c) |
|---|---|---|---|
| compound mixture | 0.1% | 5% | 15% |
| polyethylene glycol 200 | 1.0% | 2% | 3% |
| highly dispersed silica | 0.9% | 1% | 2% |
| inorganic carrier (⌀ 0.1–1 mm) e.g. CaCO$_3$ or SiO$_2$ | 98.0% | 92% | 80% |

The finely ground compound mixture is uniformly applied in a mixer to the kaolin moistened with polyethylene glycol. Non-dusty coated granulates are obtained in this manner.

| F5. Extruder granulates | a) | b) | c) | d) |
|---|---|---|---|---|
| compound mixture | 0.1% | 3% | 5% | 15% |
| sodium ligninsulfonate | 1.5% | 2% | 3% | 4% |
| carboxymethyl cellulose | 1.4% | 2% | 2% | 2% |
| kaolin | 97.0% | 93% | 90% | 79% |

The compound mixture is mixed with the adjuvants and the mixture is moistened with water. This mixture is extruded and then dried in a stream of air.

| F6. Dusts | a) | b) | c) |
|---|---|---|---|
| compound mixture | 0.1% | 1% | 5% |
| talcum | 39.9% | 49% | 35% |
| kaolin | 60.0% | 50% | 60% |

Ready for use dusts are obtained by mixing the active ingredient with the carriers on a suitable mill.

| F7. Suspension concentrates | a) | b) | c) | d) |
|---|---|---|---|---|
| compound mixture | 3% | 10% | 25% | 50% |
| ethylene glycol | 5% | 5% | 5% | 5% |
| nonylphenol polyethoxylate (15 mol EO) | — | 1% | 2% | — |
| sodium ligninsulfonate | 3% | 3% | 4% | 5% |
| carboxymethyl cellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground compound mixture is intimately mixed with the adjuvants to give a suspension concentrate from which suspensions of any desired concentration can be prepared by dilution with water.

The following Examples illustrate the ability of the safeners of formula IIa or IIb to protect cultivated plants from the phytotoxic action of herbicides of formula I.

Biological Examples

Example B1: Under greenhouse conditions, barley is cultivated in plastic pots to the 4-leaf stage. In this stage, the herbicide of Table 1 alone as well as the mixtures of the herbicide with the safener are applied to the test plants. Application is made in the form of an aqueous suspension of the test compounds in 500 l of water/ha. The rates of application of the herbicide are 60, 30 and 15 g/ha, and of those of the test safeners are 125 g/ha. Percentage evaluation is made 3 weeks after application according to the rating:
100%=test plant withered
0%=no phytotoxic action.

Examples showing that the damage caused by the safeners to barley and wheat can be markedly reduced are given in Table B1:

TABLE B1

Percentage phytotoxicity in barley with the herbicide of formula Ib alone and in combination with the compounds of formulae IIa and IIb at 125 g/ha

| Herbicide | Safener, 125 g/ha | Herbicide concentration in [g/ha] | | |
|---|---|---|---|---|
| | | 60 | 30 | 15 |
| 1.03 | — | 85 | 70 | 50 |
| 1.03 | 3.01 | 40 | 25 | 15 |
| 1.03 | 2.01 | 55 | 40 | 25 |

Examples B2 and B3: Under greenhouse conditions, barley is cultivated in plastic pots to the 4-leaf stage. In this stage, each of the herbicides 1.02, 1.03, 1.04, 1.05, 1.08 and 1.09 alone as well as the mixtures of the herbicides with the test safeners 2.01 and 3.01 are applied to the test plants. Application is made in the form of an aqueous suspension of the test compounds in 500 l of water/ha. The rates of application of the herbicide are 250, 125, 60, 30, 15 and 8 g/ha, and those of the safener are 60 and 30 g/ha. Percentage evaluation is made 3 weeks after application according to the rating:
100%=test plant withered
0%=no phytotoxic action.

Examples showing that the damage caused by the safeners to barley and wheat can be markedly reduced are given in Tables B2 and B3:

TABLE B2

Percentage phytotoxicity in barley and wheat with the herbicide of formula Ib alone and in combination with the safeners of formulae IIa and IIb at 60 g/ha

| Herbicide | Safener 60 g/ha | Barley | | | | | | Wheat | | | | | |
|---|---|---|---|---|---|---|---|---|---|---|---|---|---|
| | | Herbicide concentration in [g/ha] | | | | | | | | | | | |
| | | 250 | 125 | 60 | 30 | 15 | 8 | 250 | 125 | 60 | 30 | 15 | 8 |
| 1.05 | — | 20 | 10 | 0 | 0 | — | — | 30 | 10 | 0 | 0 | — | — |
| 1.05 | 3.01 | 0 | 0 | 0 | 0 | — | — | 10 | 0 | 0 | 0 | — | — |
| 1.05 | 2.01 | 10 | 0 | 0 | 0 | — | — | 10 | 0 | 0 | 0 | — | — |
| 1.03 | — | — | 98 | 95 | 65 | 60 | — | — | 20 | 0 | 0 | 0 | — |
| 1.03 | 3.01 | — | 85 | 15 | 0 | 0 | — | — | 0 | 0 | 0 | 0 | — |
| 1.03 | 2.01 | — | 90 | 75 | 30 | 0 | — | — | 0 | 0 | 0 | 0 | — |

TABLE B3

Percentage phytotoxicity in barley and wheat with the herbicide of formula Ib alone and in combination with the safeners of formulae IIa and IIb at 30 g/ha

| Herbicide | Safener 30 g/ha | Barley | | | | | Wheat | | | | |
|---|---|---|---|---|---|---|---|---|---|---|---|
| | | Herbicide concentration in [g/ha] | | | | | | | | | |
| | | 125 | 60 | 30 | 15 | 8 | 125 | 60 | 30 | 15 | 8 |
| 1.04 | — | 80 | 60 | 25 | 15 | 10 | 65 | 35 | 10 | 0 | 0 |
| 1.04 | 3.01 | 45 | 35 | 5 | 0 | 0 | 5 | 0 | 0 | 0 | 0 |
| 1.04 | 2.01 | 80 | 60 | 25 | 5 | 0 | 5 | 0 | 0 | 0 | 0 |
| 1.08 | — | 55 | 45 | 30 | 10 | 5 | 5 | 0 | 0 | 0 | 0 |
| 1.08 | 3.01 | 20 | 10 | 5 | 0 | 0 | 0 | 0 | 0 | 0 | 0 |
| 1.08 | 2.01 | 35 | 25 | 15 | 5 | 0 | 0 | 0 | 0 | 0 | 0 |
| 1.02 | — | 65 | 40 | 5 | 0 | — | 25 | 10 | 5 | 0 | — |
| 1.02 | 2.01 | 45 | 10 | 0 | 0 | — | 15 | 5 | 0 | 0 | — |
| 1.09 | — | — | 90 | 80 | 45 | 40 | — | 98 | 85 | 55 | 35 |
| 1.09 | 2.01 | — | 90 | 55 | 30 | 0 | — | 75 | 45 | 0 | 0 |

What is claimed is:
1. A composition for the selective control of weeds in crops of cultivated plants, comprising, in addition to inert carriers and adjuvants, as active component a mixture of
   a) a herbicidally effective amount of a N-phenylsulfonyl-N'-triazinylurea of formula I

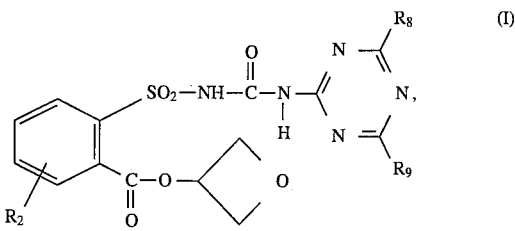

wherein
$R_2$ is hydrogen, fluoro, chloro, bromo, iodo, $(O)_nR_3$, $NO_2$, $NR_4R_5$, —C≡$CR_6$,

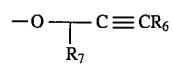

or cyano;
n is 0 or 1;
$R_3$ is $C_1$-$C_4$alkyl or $C_1$-$C_4$alkyl which is substituted by 1 to 4 halogen atoms, $C_1$-$C_3$alkoxy or $C_1$-$C_3$alkylthio; $C_2$-$C_4$alkenyl or $C_2$-$C_4$alkenyl which is substituted by 1 to 4 halogen atoms;

$R_4$ is hydrogen, $CH_3O$, $CH_3CH_2O$ or $C_1$-$C_3$alkyl;
$R_5$ is hydrogen or $C_1$-$C_3$alkyl;
$R_6$ is hydrogen, methyl or ethyl;
$R_7$ is hydrogen or methyl;
$R_8$ is $C_1$-$C_4$alkyl, $C_1$-$C_4$alkoxy, $C_1$-$C_4$haloalkoxy, $C_1$-$C_4$haloalkyl, $C_1$-$C_4$haloalkylthio, $C_1$-$C_4$alkylthio, halogen, $C_2$-$C_5$alkoxyalkyl, $C_2$-$C_5$alkoxyalkoxy, amino, $C_1$-$C_3$alkylamino or di($C_1$-$C_3$alkyl)amino; and
$R_9$ is $C_1$-$C_4$alkoxy, $C_1$-$C_4$haloalkoxy, $C_1$-$C_4$haloalkylthio, $C_1$-$C_4$alkylthio, $C_2$-$C_5$alkoxyalkyl, $C_2$-$C_5$alkoxyalkoxy, $C_2$-$C_5$alkylthioalkyl or cyclopropyl; with the proviso that $R_8$ and $R_9$ are not $OCHF_2$ and $SCHF_2$;
and b) an antidotally effective amount of a safener to antagonise the herbicide, said safener selected from the group consisting of:

a quinoline derivative of formula IIa

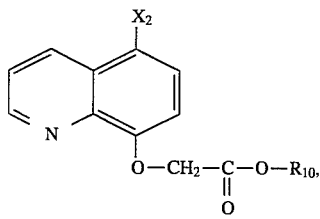

wherein
$R_{10}$ is hydrogen, $C_1$-$C_8$alkyl or $C_1$-$C_8$alkyl which is substituted by $C_1$-$C_6$alkoxy or $C_3$-$C_6$alkenyloxy; and
$X_2$ is hydrogen or chloro; and
a 1-phenylazole-3-carboxylic acid derivative of formula IIb

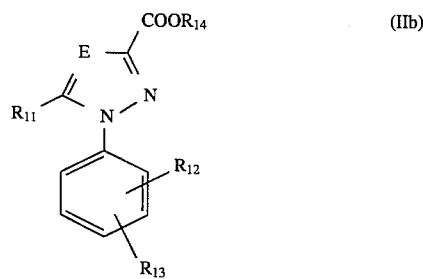

wherein
E is nitrogen or methine;
$R_{11}$ is —$CCl_3$, phenyl or halogen-substituted phenyl;

$R_{12}$ and $R_{13}$ are each independently of the other hydrogen or halogen; and $R_{14}$ is $C_1$-$C_4$alkyl; with the proviso that $R_2$ is not hydrogen when the safener consists of a compound of formula IIb.

2. A composition according to claim 1, wherein $R_8$ is methyl and $R_9$ is methoxy.

3. A composition according to claim 1, wherein the safener is a compound of formula IIa.

4. A composition according to claim 3, wherein $X_2$ is chloro.

5. A composition according to claim 3, wherein $R_{10}$ is the group —$CH(CH_3)$—$C_5H_{11}$—n or —$CH(CH_3)$—$CH_2$—O—$CH_2CH$=$CH_2$.

6. A composition according to claim 1, which comprises a compound of formula IIe

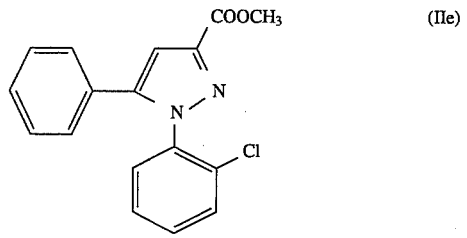

as safener.

7. A method of selectively controlling weeds and grasses in crops of cultivated plants, which comprises treating said plants, the seeds or the locus thereof, concurrently or separately, with an effective amount of a composition according to claim 1.

8. A method according to claim 7, wherein the cultivated plants are cereals.

9. A method of selectively controlling weeds and grasses in crops of cultivated plants, which comprises treating said plants or areas intended for cropping with cultivated plants, with a composition according to claim 1, wherein the N-phenylsulfonyl-N'-triazinylurea herbicide in said composition is applied at a rate of 0.001 to 2 kg/ha and the safener in said composition is applied at a rate of 0.001 to 0.5 kg/ha.

10. A composition according to claim 1, wherein $R_2$ is selected from the group consisting of 5—$OCH_3$, 5—$OCH_2H_5$ and 5—$OCHF_2$.

* * * * *